United States Patent
Dobrzynski et al.

(10) Patent No.: US 11,433,101 B2
(45) Date of Patent: Sep. 6, 2022

(54) PROLINE-RICH POLYPEPTIDE COMPLEX FOR USE IN TREATMENT OF BDNF-DEPENDENT DISORDERS

(71) Applicant: GEO-POLAND SP. Z.O.O., Poznan (PL)

(72) Inventors: Wlodzimierz Piotr Dobrzynski, Poznan (PL); Magdalena Anna Bednarek, Poznan (PL)

(73) Assignee: Geo-Poland sp. z o.o., Poznan (PL)

( * ) Notice: Subject to any disclaimer, the term of this patent is extended or adjusted under 35 U.S.C. 154(b) by 250 days.

(21) Appl. No.: 16/917,814

(22) Filed: Jun. 30, 2020

(65) Prior Publication Data

US 2021/0015871 A1 Jan. 21, 2021

Related U.S. Application Data

(63) Continuation of application No. 15/524,601, filed as application No. PCT/PL2015/000180 on Nov. 2, 2015, now abandoned.

(30) Foreign Application Priority Data

Nov. 4, 2014 (PL) ........................ 410058

(51) Int. Cl.
- *A61K 35/20* (2006.01)
- *A23C 9/20* (2006.01)
- *A23L 33/18* (2016.01)
- *A23L 33/00* (2016.01)

(52) U.S. Cl.
CPC .............. *A61K 35/20* (2013.01); *A23C 9/206* (2013.01); *A23L 33/18* (2016.08); *A23L 33/40* (2016.08)

(58) Field of Classification Search
None
See application file for complete search history.

(56) References Cited

PUBLICATIONS

PL218693B1 (English translation provided by Google Patents). (Year: 2015).*
Sokolowska, et al., International Dairy Journal, 18:204. (Year: 2008).*

* cited by examiner

*Primary Examiner* — Michael Barker
(74) *Attorney, Agent, or Firm* — Phillips Lytle LLP; David L. Principe

(57) ABSTRACT

The invention relates to the Proline-Rich Polypeptide complex (PRP) derived from the mammalian colostrum for use in the treatment of the disorders and conditions related to the alterations of the Brain-Derived Neurotrophic Factor level as well as modulation thereof, particularly disorders and conditions wherein therapeutic strategy is based on the increasing of the BDNF concentration in blood.

The PRP complex is postulated to be used for nutrition of adults, young children/babies and infants to promote and preserve the proper development and function of both immune and nervous system. PRPs may be used for supplementation of modified milk and infant milk formulae to make it closer to breast milk.

17 Claims, 5 Drawing Sheets

PROLINE-RICH POLYPEPTIDE COMPLEX FOR USE IN TREATMENT OF BDNF-DEPENDENT DISORDERS

FIELD OF THE INVENTION

The present invention relates to the Proline-Rich Polypeptide complex derived from the mammalian colostrum for use in the treatment of the disorders and conditions related to the alterations of the Brain-Derived Neurothropic Factor level as well as modulation thereof. In particular, the invention concerns the use of the Proline-Rich Polypeptide complex in the prophylactic and auxiliary treatment of the disorders and conditions responding to the increase of BDNF levels.

Proline-Rich Polypeptide complex is intended to be used for nutrition of adults, young children/babies and infants to promote the proper development and function of both immune and nervous system. Furthermore, the complex could be used for the supplementation of the infant milk formula thus making it closer to breast milk.

BACKGROUND OF THE INVENTION

It has been well documented in the art that mammalian colostrum is a rich source of health-enhancing components including the immune system supporting factors. Colostrum, the pre-milk fluid produced by mammals during the first 72 hours after birth, contains a high concentration of various constituents, e.g. nutritional factors, immunoglobulins, growth factors, cytokines and the specific immune cells, such as lymphocytes T, lymphocytes B, neutrofiles, and macrophages (Borysewicz-Sańczyk and Szczepański. Postepy neonatologii. 15(1), 2009, in Polish).

The Proline-Rich Polypeptide complex (PRP) was originally isolated from the ovine colostrum by Janusz et al., FEBS Lett. 49 (2), 1974. That colostrum-derived Proline-Rich Polypeptide complex has been characterized to have a molecular weight of 18.000 Daltons, and includes three non-covalently linked subunits. It has about 22 percent proline content, and is referred to as colostrinin. Later on, the analogues of PRPs were identified in the other types of mammalian colostrum.

Studies of human peripheral blood mononuclear cells have evidenced that Proline-Rich Polypeptide complex stimulate blood cells to release the key immune system cytokines, eg., INF-$\gamma_y$, TNF-$\alpha$, 1L-6, and IL-1$\beta$, thus boosting or inhibiting the immune system (restoring the homeostasis). Moreover, the PRP preparations could accelerate the maturation and differentiation of murine thymocytes to active lymphocytes.

Well-defined biological activity of Proline-Rich Polypeptide complex along with the long-term studies concerning the pathogenesis of Alzheimer's disease, and particularly confirmed inhibitory effects of cytokines and interleukins on amyloid-$\beta$ peptides (A$\beta$) aggregation (Griffin et al. Brain Pathol. 8(1), 1998), suggest that PRPs may find use in multiple neurogenerative disorders. However, the mechanism underlying alleged neuroprotective effects of PRPs in Alzheimer's disease is still unknown. Alzheimer's disease is a form of dementia, characterized by the broad array of pathological conditions, leading to the progressive impairment of brain function, including memory loss symptoms, the rationality, the routine. Approximately 50-70% of all cases of dementia is due to the neurological abnormalities in the brain, including formation of senile plaques composed of A$\beta$, as a result of proteolytic clevage of amyloid beta precursor ($\beta$APP) involving secretases activity, and tau protein hyperphosphorylation followed by neurofibrillary tangles (NFT) formation.

In vivo studies have proved also the psychotropic activity of the Proline-Rich Polypeptide complexes. The administration of Proline-Rich Polypeptide complex boosted cognitive functions in aged rats and was shown to facilitate acquisition of spatial learning and improved incidental memory in aged rodents in the manner similar to that observed in the young animals (Popik et al., Pharmacol. Biochem. Behav. 64 (1), 1999).

Due to the pivotal role of the Proline-Rich Polypeptide complexes in stimulation growth, proliferation and differentiation of neurons by the PRP-mediated increased gene expression, PRPs might find use in the tissues regeneration and skin disorders treatment. There is some indication that Proline-Rich Polypeptide complexes accelerate growth and regeneration of damaged neurons in Central Nervous System, that are critical processes for pathological changes typical for neurodegenerative disorders progress.

The effect of the Proline-Rich Polypeptide complex on the improvement of the cognitive function was also investigated. Most of the information related to the pro-cognitive activity of PRPs was obtained from the animal models, young and old rats, chicks, as well as three clinical trials with Alzheimer's disease patients. In vitro studies proved the strong activity of Proline-Rich Polypeptide complex in diminishing amyloid-$\beta$ peptides toxicity in the primary neuronal cell culture by reducing the level of an antioxidative enzyme, superoxide dismutase 1 (SOD1) (Froud et al. J. Alzheimers Dis. 20 (2), 2010).

Furthermore, it has been shown that the Proline-Rich Polypeptide complex itself is non-allergenic and may even prevent inflammations induced by environmental allergens.

Anti-oxidative activity of the Proline-Rich Polypeptide complex is well documented. Results from several studies indicate that PRPs inhibit nitric oxide (NO) formation in cell culture and decrease the generation of intracellular reactive oxygen species (ROS) and oxidative stress, retarding the aging process and protecting from neuronal loss. Both, in vitro and in vivo studies have shown that PRPs significantly decelerate the senescence of cultured cells and extends the lifespan of cells isolated from senescence-accelerated mice. It was documented that PRPs may delay the cellular aging process by decreasing sequence alterations in DNA in human and in Chinese hamster cell cultures. Further studies have revealed that PRPs show an antimutagenic action in cells stressed oxidatively or exposed to two chemical mitotic agents, methyl methanesulfonate and mitomycin C, commonly used in cancer treatment. Noteworthy, Proline-Rich Polypeptide complex decreases UVA- and UVB-induced mutation frequency responsible for development of malignant melanoma and squamous cell carcinoma, respectively.

These data along with the well-documented high immunotropic activity of colostrinin in vitro in blood samples of patients with numerous disorders may suggest the possible usage of the Proline-Rich Polypeptide complex as an active agent to treat chronic diseases with a bacterial and viral etiology, and acquired immunological deficiencies in the aftermath of chemo- and radiotherapy as set forth in the Polish Patent PL 185442 B1.

International Patent Application published as WO 98/14473 disclosed the use of colostrinin for CNS disorders treatment, such as neurological disorders, mental disorders, dementia, neurodegenerative diseases, psychosis, neurosis, and especially Alzheimer's disease. It has been suggested that colostrinin might be used to ameliorate immune system development in infants as well as to counter immunological deficiencies in babies. The specification of WO 98/14473 discloses the oral pharmaceutical compositions of colostrinin as a dietary supplement for the treatment of infants, children and adults undergoing the chemotherapy and/or adults suffered from cachexia or chronic disorders-evoked excessive loss of body weight.

International Patent Application published as WO 00/75173 provides the colostrinin-derived peptides sequences, the said peptides being useful, inter alia, in the treatment of disorders of the immune system and the central nervous system.

Patent specification EP 1238058 B1 discloses the use of the constituent peptides of colostrinin as the neural cell differentiation promoters in vitro.

In the International Patent Application WO02/13851, colostrinin, constituent peptides thereof, and proline rich active analogues of colostrinin are described as promoters of neural cell differentiation, e.g. pluripotent cells of the nervous system, in vitro and in vivo. Using PC12 cells, it has been investigated the influence of colostrinin and its analogues to convert the damaged neuronal cells to functional neurons, process being strongly associated with the neuronal cell differentiation accompanied by the neurotrophic factors production, including Nerve Growth Factor (NGF).

The US patent application US 2011/0098216 discloses the use of colostrinin for prevention and/or treatment of obesity and obesity-related comorbidities, including type II diabetes mellitus, hypercholesterolemia, atherosclerosis, coronary heart disease, stroke, infammatory conditions, such as, but not limited to, irritable bowel syndrome, infammatory bowel disease, including Crohn's disease. These beneficial therapeutical effects were assigned to the colostrinin-dependent regulation of the gene expression of both, leptin and resistin, in cells.

The Proline-Rich Polypeptide complex of another composition has been isolated from bovine colostrum produced during the first 48 hours after birth with the use of the innovative technology described in the Polish patent PL 218693 B1. The said technology consisted of the acetone extraction of polypeptide mixture from colostrum, to obtain the unique complex substance referred to as COLOCO prp. The structure of COLOCO prp complex is slightly different from the prior art Proline-Rich Polypeptide complex composition, and refers to the peptide mixture of low molecular weights to 10 kDa, containing about 20 percent of proline, and characterized by the presence of high proportion of acidic amino acids (~18%), the non-biological active β-lactoglobulin (17 kDa) fraction, as well as the associated non-peptide components that do not exert their own biological activity.

In vitro studies using the peripheral blood mononuclear cells have revealed the ability of COLOCO prp to stimulate cytokines, such as IL-β and IL-6, production and this effect was similar to the effect of reference colostrinin isolated from the colostrum according to the method previously described by Janusz et al. (FEBS LETTERS, 49, 276-279, 1974).

Further in vitro studies have shown that COLOCO prp inhibits NO generation and attenuates the oxidative stress comparably to the reference product (bovine or/and ovine colostrinin) in a model of peripheral blood mononuclear cells. This effect was estimated using Trolox equivalent antioxidant capacity (TEAC) method.

The own research have demonstrated the ability of COLOCO prp to attenuate Aβ aggregation under abiotic conditions. Incubation of Aβ monomers with COLOCO prp effectively blocked Aβ fibrill formation in a concentration-dependent manner as well as disrupted the pre-aggregated Aβ fibrillar structure thus making it effective in preventing both early and advanced neurodegenerative changes typical for Alzheimer's disease.

In view of the previously published data, the colostrum-derived Proline-Rich Polypeptide complexes have the capacity to modulate immune system function, and have the anti-inflammatory and anti-oxidative activity combined with their neuroprotective properties. However, any empirical results of the investigation of the correlation between these beneficial therapeutical effects and the purely medical mechanism(s) of action of the PRP preparations have not been known to date.

DISCLOSURE OF INVENTION

The present invention is based on the results of the experimental studies conducted by the present Inventors, demonstrating the effect of the Proline-Rich Polypeptide complex treatment on the Brain-Derived Neurotrophic Factor serum levels in healthy individuals.

Brain-Derived Neurotrophic Factor (BDNF) is a member of the nerve growth factor family, which has a prominent role in maturation and differentiation of neurons and glial cells. It has been well documented that BDNF expression is significantly increased in response to toxic agents, e.g. Aβ, providing neuroprotection. BDNF seems to be the best characterized neurotrophin in terms of its role in the proper neural system activity. Therefore, BDNF is thought to be an appropriate biomarker to investigate the brain pathology of autoimmune diseases, e.g. multiple sclerosis, and many other neurological disorders, including Alzheimer's disease, Huntington's disease, and Parkinson's disease.

BDNF level is highly associated with the immune deficiency syndrome, including human immunodeficiency virus (HIV). It has been shown that memantine, which has been recently approved for the treatment of Alzheimer's disease, prevented onset of cognitive deficits in the brain and this effect was correlated with the memantine-mediated upregulation of BDNF expression. Moreover, increased expression of BDNF within the brain led to the enhancement of dopamine and serotonine concentration in the brain. Thus, BDNF synthesis is regarded as an anti-depressant activity. Several data showed that inflammation accompanied by exaggerated pro-inflammatory cytokine production have been implicated in the pathogenesis of depression-like behaviour. In these conditions, BDNF level is strongly reduced in selected areas of the brain, accelerating depression-like symptoms. Thus, treating depression patients with BDNF constitute an effective therapy of mood-related neuropsychiatric diseases.

BDNF secretion is also observed in several non-neural tissues, being mainly expressed in response to pathological conditions in the brain. BDNF acts as a specific inducer of the activity of immune system cells, such as lymphocytes and monocytes, and stimulates macrophages migration to the region of the brain with lesion to activate the regeneration process.

BDNF has been shown to regulate food intake-behavior, glucose and lipids metabolism and body weight maintenance. Reduced concentration of blood BDNF is often associated with eating disorders.

Several data indicate that reduction of BDNF level in the hippocampus occurs during aging, and is associated with cognitive decline, while both, exercise and diet, appear to increase hippocampal BDNF expression and impede age-associated memory deficits.

BDNF, like other neurotrophic factors, mediates many activity-dependent processes in the mammalian brain, including neuronal differentiation and growth, synapse formation and plasticity, and myelination (Park and Poo, Nat Rev. Neurosci. 14(1), 2013). Together with these functions, BDNF is highly correlated with the onset of various diseases including multiple sclerosis. Previous findings indicate that BDNF is protective against focally demyelinated nerves, and increased brain BDNF expression in multiple sclerosis is related to the enhancement of remyelination process.

According to Nassar et al. study (Matern. Child. Nutr. 7(2), 2011), blood BDNF level might vary depending on infant feeding pattern as assessed using Bayley Scale of Infant Development-second edition (BSID-II). This study revealed that breastfed group had higher BSID-II scores followed by mixed-fed group then formula-fed one, yet these results reached statistical significance only in total behaviour rating scale (TBRS) and Motor Quality Percentile rank values. Additionally, breastfed infants had significantly higher values of serum BDNF when compared to those receiving formula milk, and this positive correlation is believed to be due to benefits of breastfeeding as a process that may trigger the secretion of BDNF because it is the best pleasurable peaceful situation for the infant.

There is some evidence that BDNF naturally occurs in the milk of lactating women, being produced by some type of cells, e.g. leucocytes. This study reports changes in BDNF levels during lactation, and is constant from 3 to 90 day of lactation. Additionally, BDNF level is higher in maternal milk than in serum of lactating women, indicating its crucial role in an infant diet.

In view of this knowledge, regular infant milk formulae available on the market seem to be insufficient for the proper development of infants.

There is a growing social need for specific biological agents that could positively stimulate the development and maintain the function of the immune as well as the nervous system, and due to their natural origin would be safe for use and standardized at the same time, thus providing the beneficial effects in both adults and children.

That need could be satisfied by the use of the biological agent according to the present invention, which may affect the vital immune system support combined with the neuroprotective effects when administered at the specific dosage regime.

The present invention provides the Proline-Rich Polypeptide complex derived from the mammalian colostrum for use in the treatment of disorders and conditions related to the alterations of the Brain-Derived Neurotrophic Factor level as well as modulation thereof.

"Treatment", as used herein, comprises therapeutic, prophylactic as well as auxiliary treatment of the conditions and disorders responding to the modulation of the Brain-Derived Neurotrophic Factor level.

The term "modulation of the Brain-Derived Neurotrophic Factor", as used herein, relates both to increasing BDNF serum concentration induced by the Proline-Rich Polypeptide complex to the level necessary to maintain the proper function of immune and nervous system, as well as to prevent from temporary BDNF fluctuations triggered by environmental factors, e.g. inadequate nutrition, tiredness or chronic stress.

The research on healthy adult individuals carried out by the present Inventors demonstrated that administration of the Proline-Rich Polypeptide complex leads to the significant increase of BDNF level in human serum.

On the basis of that own research outcomes referring to the PRP-induced BDNF level augmentation, as described in the experimental part of the present description, along with the common scientific knowledge confirming the strong correlation between depleted peripheral BDNF level and the onset of various conditions and disorders, it is postulated that administration of the Proline-Rich Polypeptide complex may prevent the development of these pathological conditions and disorders in adults and children.

In one aspect of the present invention, the Proline-Rich Polypeptide complex is intended for use in the treatment of disorders selected from a group comprising, without limitation, mental disorders, including mood disorders, obsessive-compulsive disorders, major depression; Parkinson's disease; Huntington's disease, Alzheimer's disease; spinocerebellar ataxia; disorders induced by the human immunodeficiency virus (HIV); diabetes mellitus; eating disorders, including anorexia nervosa and bulimia nervosa; obesity and obesity-related disorders; glaucoma; retinal abnormalities; central nervous system demyelinating diseases, including multiple sclerosis; peripheral neuropathy; cerebrovascular diseases, including stroke; migraine and other headache syndromes, cardiovascular diseases and others.

Another aspect of the present invention provides the use of the Proline-Rich Polypeptide complex in the treatment of disorders related to malfunctions of the nervous system or temporary intensive mental activity, depressed mood, memory decline, concentration and memory difficulties, and tiredness, to ensure the proper functioning of the nervous system and maintaining the activity of the BDNF-dependent neurons.

Anti-radical protection activity of the Proline-Rich Polypeptide complex together with its capacity to regulate BDNF level in blood indicate that PRPs may be useful as a cognitive and attention enhancer, particularly applicable to individuals with mild cognitive deficits.

Another aspect of the invention provides the Proline-Rich Polypeptide complex for prophylactic use to improve cognitive functions and enhance the nervous system development of infants and young children. Well-defined role of BDNF in infant development, particularly in an early stage of life, along with PRPs capacity to increase BDNF level, suggest that Proline-Rich Polypeptide complex may serve as a specific activator of myelin formation in infants and young children, thereby contributing the nervous system development.

In the specific embodiment of that aspect of the invention, the Proline-Rich Polypeptide complex is intended to be used as a nutritional additive/supplement for infants and young children, particularly to the milk formulae fed infants who had not been breast fed from birth and who have been deprived of Proline-Rich Polypeptide complex. Feeding the infants with the modified milk formulae enriched with PRPs, as the sole milk source or in combination with breastfeeding, increases the level of BDNF in babies' blood comparable to the BDNF level detected in only breastfed infants.

The present invention further provides the modified infant milk formulae enriched with the Proline-Rich Polypeptide complex derived from the bovine colostrum, preferably with the Proline-Rich Polypeptide complex comprising from 16 to 22 percent proline.

The unique composition of the modified infant milk formula enriched with bovine-derived Proline-Rich Polypeptide complex that makes it closer to breast milk is hereinafter referred to as Coloco Mathernized Formula (CMF). The novel composition of CMF shows the unique properties to increase the BDNF level in the infants' blood.

In the preferred embodiment of the invention, the modified infant milk formula is intended to be administrated in an amount meeting daily infant's requirement for PRPs within the range of 1 to 5 micrograms per 1 kilogram of body weight.

CMF composition disclosed in the present invention provides the circulating BDNF level comparably or even higher to the level detected in the blood of breastfed babies, thereby supporting the development of the nervous system. Enrichment of the infant milk formulae with Proline-Rich Polypeptide complex, especially with Proline-Rich Poypeptide complex free of IgG, decides to its additional beneficial effect on the immune system of babies, involving immunomodulation, the general immunity improvement, anti-allergic effects, and protection from the autoimmunoaggression.

Nutritional composition of CMF according to the present invention is far more beneficial for babies' health than regular milk formulae available on the market as enrichment of the infant formula with PRPs increases the circulating BDNF concentration similarly to the BDNF level detected in the blood of only breastfed babies.

Another aspect of the invention provides the Proline-Rich Polypeptide complex for use as a nutritional additive for pregnant women, in order to increase the BDNF level in the blood of a mother and a baby. The pregnant women diet enriched with PRPs contributes to the activation of immunomodulatory and anti-allergic processes as well as leads to the improvement of the general immunity.

Further aspect of the present invention provides Proline-Rich Polypeptide complex for use as a nutritional additive for older babies after breastfeeding and/or after milk formula feeding, and for adults, in order to induce and/or enhance the activity of nervous system and/or to achieve the pro-cognitive effect, ie. the memory and concentration improvement.

DETAILED DESCRIPTION OF THE INVENTION

Figure 1:
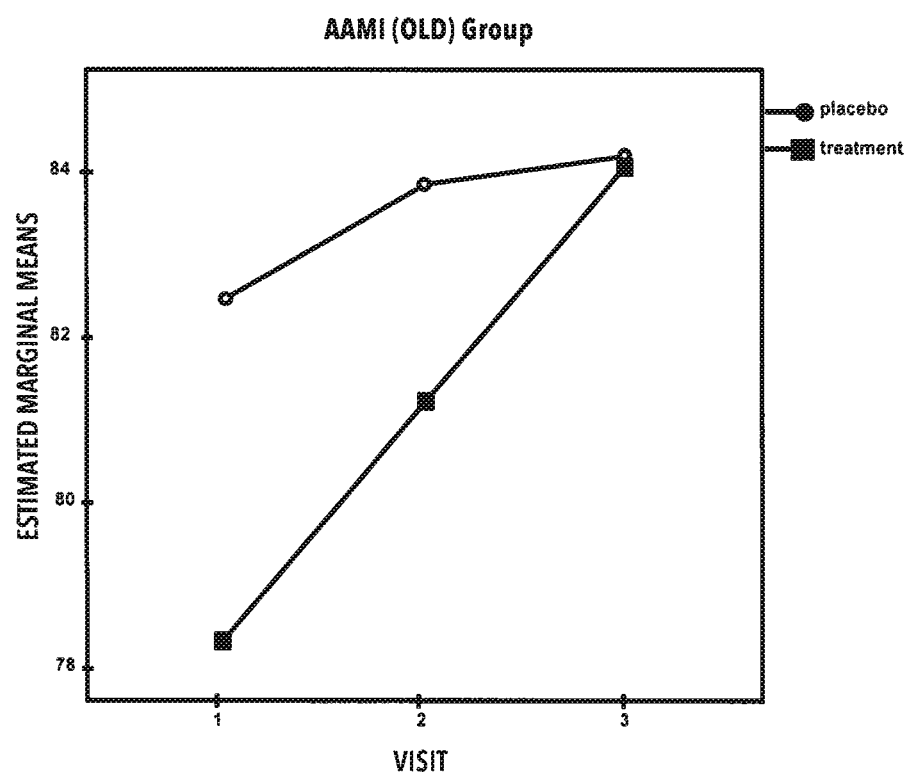
FIG. 1 is a graph illustrating the difference in the changes of DMS (Delayed Match to Sample), Percent Correct in the system of intra-group measurements between visits for the AAMI (Age-Associated Memory Impairment) group.

The Proline-Rich Polypeptide complex derived from mammalian colostrum for use according to the present invention generally refers to the complex comprising from 16 to 24 percent of amino acid residue proline, preferably 20 percent of proline.

The Proline-Rich Polypeptide complex is isolated from the big animals' colostrum, preferably from the bovine colostrum. It may be also obtained from the other mammals, including sheeps, goats and other farm animals.

In a preferred embodiment of the invention the Proline-Rich Polypeptide complex is obtained from bovine colostrum according to the method described in the Polish Patent PL 218693 BI, hereinafter referred to as COLOCO prp. The term "COLOCO prp" as used herein refers to the polypeptides mixture of low molecular weights to 10 kDa, containing from 18 to 20 percent proline, preferably 20 percent proline, and characterized by the presence of high proportion of acidic amino acids (~18%), non-biologically active β-lactoglobulin (17 kDa) fraction and concomitant non-protein components.

In another preferred embodiment of the invention, the Proline-Rich Polypeptide complex is the polypeptide mixture free of the β-lactoglobulin fraction, as isolated from the COLOCO prp by separation based on the molecular weight.

In yet another preferred embodiment of the invention, the Proline-Rich Polypeptide complex is the whey protein complex separated from the bovine colostrum according to the method described in PL 218708 B1. That whey protein complex contains cut off fractions of molecular weights below 1 kDa and from 7 to 12.5 percent proline. The use of whey protein complex in place of COLOCO prp requires re-calculation of the content of proline residues with reference to the standard content of proline (at 16 to 24%) provided in the present invention and need to be standardized along with the concomitant carrier to the correct protein level.

In use according to the invention, the Proline-Rich Polypeptide complex is intended to be administered to individuals responding to the increase of BDNF level or the modulation thereof, in a therapeutically or prophylactically effective dose level and according to the pre-determined dosage scheme.

The therapeutically or prophylactically effective daily dose of the Proline-Rich Polypeptide complex may vary depending on the specific condition or disorder to be treated, the individual's age, the body weight, the general health condition, and the expected effect of the treatment, and may be determined by the person well skilled in the art (health professional or dietician) on the basis of the clinical studies outcomes.

The therapeutically or prophylactically effective daily dose of the Proline-Rich Polypeptide complex in adults is preferably in the range of 50 to 1000 micrograms, more preferably in the range of 80 to 160 micrograms, and may be administrated once a day or may be provided in the sub-doses several times a day.

In a proposed preferred dosage scheme the Proline-Rich Polypeptide complex may be administrated to an adult within about 2 to 4 weeks period, most preferably for 4 weeks, followed by the period when the Proline-Rich Polypeptide complex administration is not recommended. The PRP-free period could be 1 to 4 weeks, most preferably 2 weeks. The dosage cycle is preferably to be repeated at least once, more preferably more than once.

Daily dose of the Proline-Rich Polypeptide complex for use for supplementation of infant milk formula and baby food is preferably in the range of 1 to 5 micrograms per 1 kilogram of body weight.

Daily dose of the Proline-Rich Polypeptide complex for use for supplementation of pregnant women's' diet is preferably in the range of 50 to 140 micrograms.

The Proline-Rich Polypeptide complex may be administrated per se in the native form isolated directly from the liquid or lyophilised colostrum, or as an ingredient of the formulation comprising the therapeutically or prophylactivcally effective dose of PRPs in association with the physiologically acceptable carrier and/or other excipients.

The Proline-Rich Polypeptide complex for use according to the present invention may be provided in various forms depending on the general health condition, the severity of disorder/disease or the target group of recipients. The Proline-Rich Polypeptide complex may be used in the form of pharmaceutical product, nutraceutic, nutritional supplement, food for special medical purposes, food for particular nutritional uses or dietary supplement.

The pharmaceutical product composition for use according to the present invention comprises an active agent, the Proline-Rich Polypeptide complex, in association with the inert and physiologically acceptable carrier and/or excipients, recommended for use within the given formulation and not exerting their own therapeutic effect nor interfering negatively with the active agent.

The pharmaceutical product composition of the Proline-Rich Polypeptide complex for use according to the present invention can be formulated in any form suitable for systemic administration. For example, for oral administration it may be formulated in the form of tablets, capsules, starch capsules, film coated tablets or enteric coated tablets; as powder or granules; as solution, oral suspension or emulsion. Tablets or capsules for oral administration comprise the traditionally used excipients such as binders, fillers, wetting agents and disintegrants. Tablets may be coated according with the commonly used methods. Oral liquid forms can be prepared as aqueous or oil suspensions, solutions and emulsions; syrups, elixirs; powders or lyophilisates for reconstitution with water or another liquid carrier ex tempore. Oral liquid formulations can include additional ingredients such as suspending agents, emulsifiers, non-aqueous carriers (such as edible oils), or preservatives. The type and amount of carriers/excipients depends on the pharmaceutical form and route of administration thereof. The suitable formulation will be prepared using techniques well known in the art, using any physiologically acceptable carriers, diluents, fillers and other excipients.

The pharmaceutical formulations of the Proline-Rich Polypeptide complex for use according to the present invention can also be formulated as nutraceutics. Nutraceutics may be used as dietary supplements or any other functional foods providing health benefits. Nutraceutics are commonly used to supplement a person's food intake with the nutrients derived from the natural food sources that are purported to provide extra health benefits. Despite the nutraceutics naturally occur in food in a very small amount, the biological importance of these substances is crucial for supporting the function of the body.

The pharmaceutical formulations for use according to the present invention can also be used as food for special medical purposes, ie. food intended for individuals with certain diseases, disorders or medical conditions whose nutritional requirements cannot be met by normal foods.

Further, the formulations for use according to the present invention can be included in the food for particular nutritional use. The term "food for particular nutritional use" refers to the foods which, due to their special composition or manufacturing process, are clearly distinguishable from food for normal consumption and are intended for individuals who suffer from specific diseases, disorders or medical conditions. In particular, nutritional use must fulfill the particular nutritional requirements of individuals whose digestive processes or metabolism are disturbed, or individuals who are in a special physiological condition and will benefit from controlled consumption of certain substances, or infants or young children in good health.

The formulations for use according to the present invention can be used as nutritional supplements that are intended to provide nutrients that may otherwise not be consumed with a diet in sufficient quantities.

Small size and simple structure of the Proline-Rich Polypeptide complex constituents, including COLOCO prp, allow the polypeptides to pass easily through the mucous membrane, especially of oral cavity and throat, as a result of ordinary diffusion or across epithelium via cell receptors for immunomodulators. Thus, the Proline-Rich Polypeptide complex can be preferably formulated for oral administration and may be provided in liquid or solid form for absorption through the mucosa of the oral/nasopharyngeal cavity and/or in the alimentary tract.

The type of suitable formulation selected for the use according to the invention will depend on the target group and the specific therapeutic use. The most preferred dosage forms according to the present invention can be prepared in the form of tablets, lozenges, sublingual tablets, pills, capsules, powders, granules, nectar/drinks or syrups. The proper dosage forms for older children may be, for example, chewing gums, bars, candies or lollipops. The proper dosage forms for pregnant women may be, for example, tablets, capsules, drops, milk drinks, beverages, chewing gums, bars, candies or others.

In the preferred embodiment of the invention, the Proline-Rich Polypeptide complex for use according to the invention is the additive of the infant milk formulae in the first year of life, the most preferably at 6 to 12 months of age.

Based on the own clinical study outcomes in healthy adult subjects, the Proline-Rich Polypeptide complex is expected to exert the similar activity, comprising the modulation of blood BDNF level, in population of infants. It is postulated that addition of the Proline-Rich Polypeptide complex to the infant milk formulae provides the proper development and function of nervous system of infants and young children in the BDNF-dependent manner. The animal toxicity study has revealed the low toxicity of the PRPs (LD50>1.25 kg/kg of body weight) thereby confirming that addition of PRPs to the infant milk formula is entirely safe.

The Proline-Rich Polypeptide complex derived from the bovine-derived colostrum, in accordance with the Decree of the Minister of Health of the Republic of Poland on the food for particular nutritional uses, is included to the group of the whey proteins recommended for nutrition of infants and young children, additionally indicating the high safety of PRP-enriched formulations.

The composition of Coloco Mathernized Formula (CMF) milk disclosed in the present invention is enriched with the Proline-Rich Polypeptide complex in an amount that meets the daily infant's requirement for PRPs within the range of 1 to 5 micrograms per 1 kilogram of body weight. This dosage level is expected to be effective in increasing the blood BDNF level in infants to the level comparable or even higher to the level detected in the blood of breastfed babies.

The Proline-Rich Polypeptide complex can be used as the sole therapeutically or prophylactically active agent or it can be administered in combination with any therapeutic agent or dietary supplement.

In one aspect of the invention, the Proline-Rich Polypeptide complex contained in the suitable pharmaceutical composition may be co-administrated with B vitamins, particularly with vitamin B1, at the dose from 0.9 mg-1.5 mg, preferably 1.1 mg per day.

In another aspect of the invention, the Proline-Rich Polypeptide complex may be administered in combination with antioxidant agents, including mitochondrial antioxidants, such as N-acetyl-L-carnitine, at the dose from 250 mg-2000 mg, preferably 1000 mg.

In another aspect of the invention, the Proline-Rich Polypeptide complex may be used in combination with the alpha lipoic acid.

Further, the Proline-Rich Polypeptide complex may be administered in combination with docosahexaenoic acid (DHA). DHA, being one of the most commonly used ingredient in infant food, is included in the group of omega-3 fatty acids with an array of health benefits such as supporting the nervous system development and contributing to the myelination process. DHA deficiency may be associated with the onset and progression of neurological disorders in children such as ADHD. Combination of PRPs with DHA may advantageously be used to the infant milk formulae supplying the neurons with the building material to myelin formation and cell membrane repair (DHA) as well as providing the specific promoter of myelination process.

In another aspect of the invention, the Proline-Rich Polypeptide complex may be administered in combination with agents showing the ability to dissolve pre-existing tau aggregates (neurofibrillary tangles, NFT) or with inhibitors of tau protein aggregation such as methylene blue.

The results from the studies conducted in healthy volunteers have evidenced that the Proline-Rich Polypeptide complex isolated from the mammalian colostrum is safe and boosts the blood BDNF level in population of healthy adults. Thus, in accordance with the present invention, the Proline-Rich Polypeptide complex may advantageously be used in the prophylactic and auxiliary treatment of the disorders and conditions related to the fluctuations of BDNF level and for modulation thereof. Particularly, the beneficial therapeutic effects are obtained due to the use of the Proline-Rich Polypeptide complex as a dietary ingredient in adults and children as well as the supplement of food and modified milk formulae for infants. Supplementation of the infant milk formulae with the Proline-Rich Polypeptide complex allows, due to its effect on the BDNF level increase in infant blood, to make its formula closer to breast milk and thereby to achieve more beneficial nutritional effects for children health than the regular formulations without PRPs available on the market. Coloco Mathernized Formula (CMF) nutritional composition will be the most valuable for health and development of babies who cannot be breastfed.

The invention is illustrated by the following examples.

EXAMPLES

Biological Studies

In the biological studies, the tested Praline-rich Polypeptide complex was COLOCO prp isolated from bovine colostrum by the method described in PL 218693 B1.

The comparison of compositions of Proline-Rich Polypeptide complexes, COLOCO prp isolated from bovine colostrum by the method described in PL 218693 B1 and ovine Colostrinin by M. Janusz et al. (FEBS LETTERS 1974, 49, 276-279), is presented in Table 1. The amino acid profile of COLOCO prp was determined by reversed phases HPLC.

TABLE 1

| Amino acid residues | Ovine colostrinin by Janusz et al. (%) | COLOCO prp complex (%) |
|---|---|---|
| Asp/Asn | 2.56 | 4.81 |
| Ser | 5.27 | 6.57 |
| Glu/Gln | 14.90 | 14.01 |
| Gly | 2.32 | 3.76 |
| His | 1.94 | 2.78 |
| Arg | 1.80 | 2.96 |
| Thr | 6.55 | 4.28 |
| Ala | 1.38 | 3.27 |
| Pro | 22.90 | 20.68 |
| Tyr | 1.62 | 2.18 |
| Val | 12.85 | 9.85 |
| Met | 3.93 | 3.24 |
| Lys | 7.16 | 4.47 |
| Ile | 2.48 | 6.36 |
| Leu | 9.60 | 8.24 |
| Phe | 4.72 | 4.31 |
| Trp | — | — |
| Cys | 1.05 | — |

Human Evidence

Double-blind, randomized study for evaluation of COLOCO prp effects on the cognitive functions was carried out on 361 individuals assigned to 3 groups based on their age (within the range 18-75). In the treatment group, COLOCO prp was administered in a single dose of 120 μg/day with the following schedule: COLOCO prp treatment (4 weeks); a 2-week hiatus; COLOCO prp treatment (4 weeks); a 2-week hiatus; COLOCO prp treatment (4 weeks) making 16-weeks study time. The same mode of administration was also used in control (Placebo) group.

Neuropsychological Assessment

The ability of COLOCO prp to affect cognitive skills of healthy subjects was assessed using the selected neuropsychological tests. The efficacy of COLOCO prp treatment was evaluated in 3 subpopulations of subjects, who were expected to obtain the highest health benefits after COLOCO prp treatment:

«Multitaskers (MT) Group», was defined as population of young adults, male and female, aged 18-25. In this group, 122 subjects who completed the study were evaluated in accordance with the following parameters: treated group or control (Placebo) group; the center of the study: Poznan or Warsaw. During the Visit 1, Multitasking Media Questionnaire (MMQ) was completed by all subjects enrolled to the study. Based on MMQ the empirical index MMI was created.

«Attention-Deficit Trait (ADT) group», was defined as population of adults, male and female, aged 25-55. In this group, 116 subjects who completed the study were evaluated in accordance with the following parameters: treated group or control (Placebo) group; the center of the study: Poznan or Warsaw. To be enrolled to the study, during the Visit 1 the Adult ADHD Self-Report Scale (ASRS-v1.1) Symptom Checklist was completed by all invited subjects.

«Age-Associated Memory Impairment Group» was defined as population of adults aged >55, male and female. In this group, 123 subjects who completed the study were evaluated in accordance with the following parameters: treated group or control(Placebo) group; the center of the study: Poznan or Warsaw. During the Visit I and Visit 3, MoCA (Montreal Cognitive Assessment) was completed by all subjects. During the Visit 1, all subjects were evaluated to be suffered from mild cognitive impairment (MCI). Based on MoCA test, subjects with the score below 26 points were not included to the study. The difference between values of MoCA test recorded on Visit 1 and 3 was also considered to assess the efficacy of COLOCO prp regimen in the AAMI group.

To assess the cognitive performance, in particular memory and attention skills, during all three visits 4 cognitive tests taken from CANTAB neuropsychological battery were applied to all subjects enrolled to the study.

In order to compare the mean scores of the research subjects, a multi-factor analysis of variance with repeated measurements in a mixed-effects model was used. If the results did not meet the assumption of the normality of distributions of variables and due to the low number of control groups, the MANOVA results were confirmed with nonparametric tests.

The graph in FIG. 1 illustrates the difference in the changes of DMS (Delayed Match to Sample). Percent Correct in the system of intra-group measurements between visits for the AAMI group. In the placebo group, the average for visit 1 is 82.5 with a standard deviation of 1,483, while in the treatment group it is 78.333 with a standard deviation of 1.508. In the case of visit 3, these values are: 84; 194 with a standard deviation of 1.359 for the placebo group, and 84.083 with a standard deviation of 1.381 for the treatment group (Visit 1 vs Visit 3, $F=3.005$; $p=0.086$, $eta2=0.24$).

Figure 2:
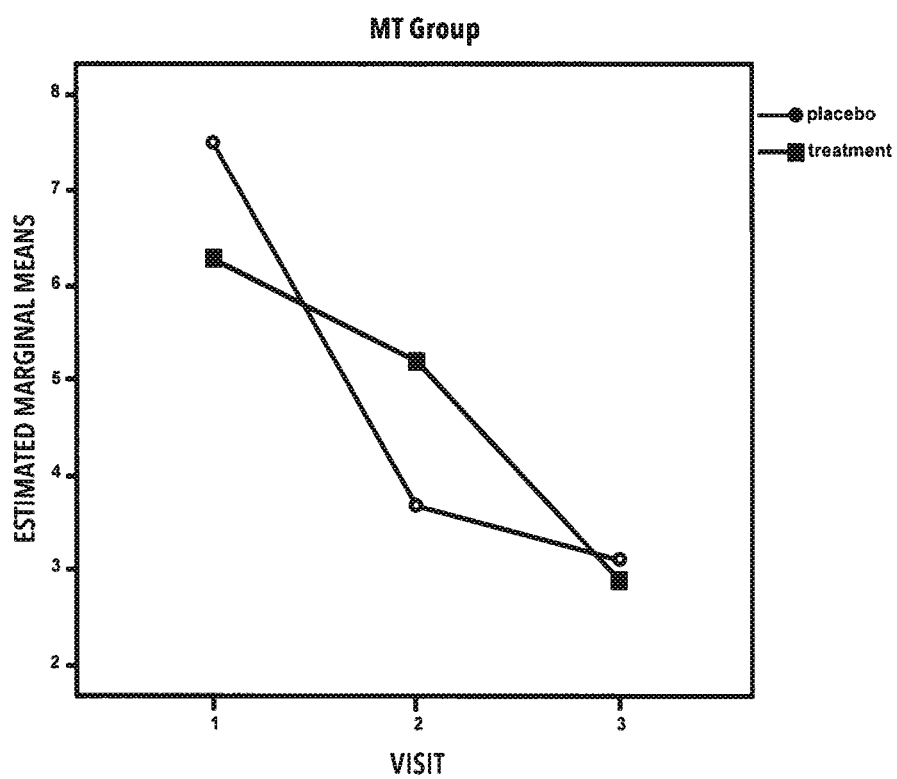
FIG. 2 is a graph showing the difference in PAL (Paired Associates Learning), with total errors (adjusted) in the system of intra-group measurements between visits for the MT (Multitaskers) group.

The graph in FIG. 2 shows the difference in PAL (Paired Associates Learning). Total errors (adjusted) in the system of intra-group measurements between visits for the MT group (the effect of repeated measurements $F=5.072$; $p=0.007$, $eta2=0.43$).

Figure 3:
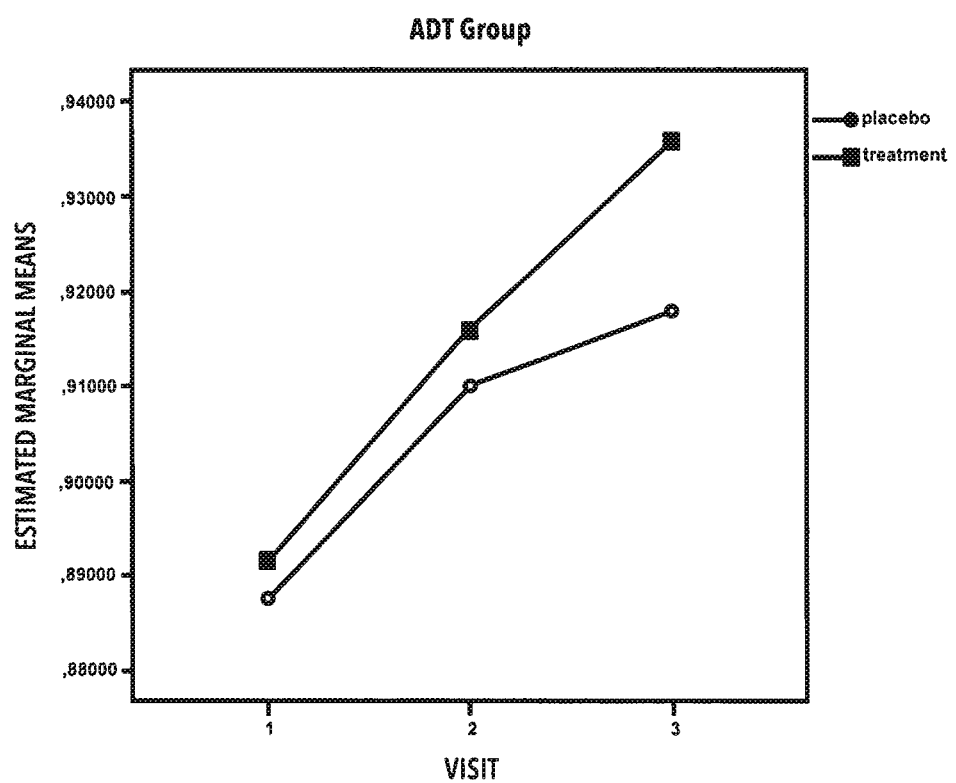
FIG. 3 is a graph illustrating the difference in the changes of RVP.A (Rapid Visual Information Processing) values in the system of intra-group measurements between visits for the ADT (Attention-Deficit Trait) group.

The graph in FIG. 3 illustrates the difference in the changes of RVP.A (Rapid Visual Information Processing) values in the system of intra-group measurements between visits for the ADT group. In the placebo group, the average for visit 1 is 0.888 with a standard deviation of 0.006, while in the treatment group it is 0.892 with a standard deviation of 0.006. In the case of visit 3, these values are: 0.918 with a standard deviation of 0.007 for the placebo group, and 0.936 with a standard deviation of 0.007 for the treatment group (Visit 1 vs Visit 3, $F=3.039$; $p=0.084$, $eta2=0.26$).

In 9 of the people aged >55 from the center in Warsaw (AAMI/OLD group) a low rate of MoCA (less than 20 points) was found during the recruitment visit, indicating significant cognitive deficits which could mean early stages of dementia—so-called MCI=Mild Cognitive Impairment After 4 months of taking COLOCO prp, these people were re-examined. In comparison to other research participants assigned to the AAMI/OLD group and taking the COLOCO prp product, the above-mentioned 9 participants displayed the highest degree of cognitive improvement. Within this group, the average value of improvement was 5 points (for some, it was as many as 9 points), compared to 3.5 points for other tests. The small number of participants in this group does not allow for a comprehensive interpretation, but it may suggest that the beneficial properties of COLOCO prp reveal themselves the most effectively in the case of strong deficits.

What confirms this reasoning is the observation related to the MT group (the youngest one). Using the Media Multitasking Questionnaire (MMQ) and calculating the Media Multitasking Index (MMI), it is possible to divide this group into the so-called Heavy Multitaskers and Light Multitaskers (they differ by one standard deviation). Again, in Warsaw among the Heavy Multitaskers from the treatment group, the average value of improvement between visit 1 and 3 is higher than in the case of Light Multitaskers. This applies to the Cognitive Performance Index (CPI), which is calculated on the basis of four tests (PAL, RTI, DMS, RVP) included in the CANTAB battery of tests. The observation focused on 4 people.

Figure 4:
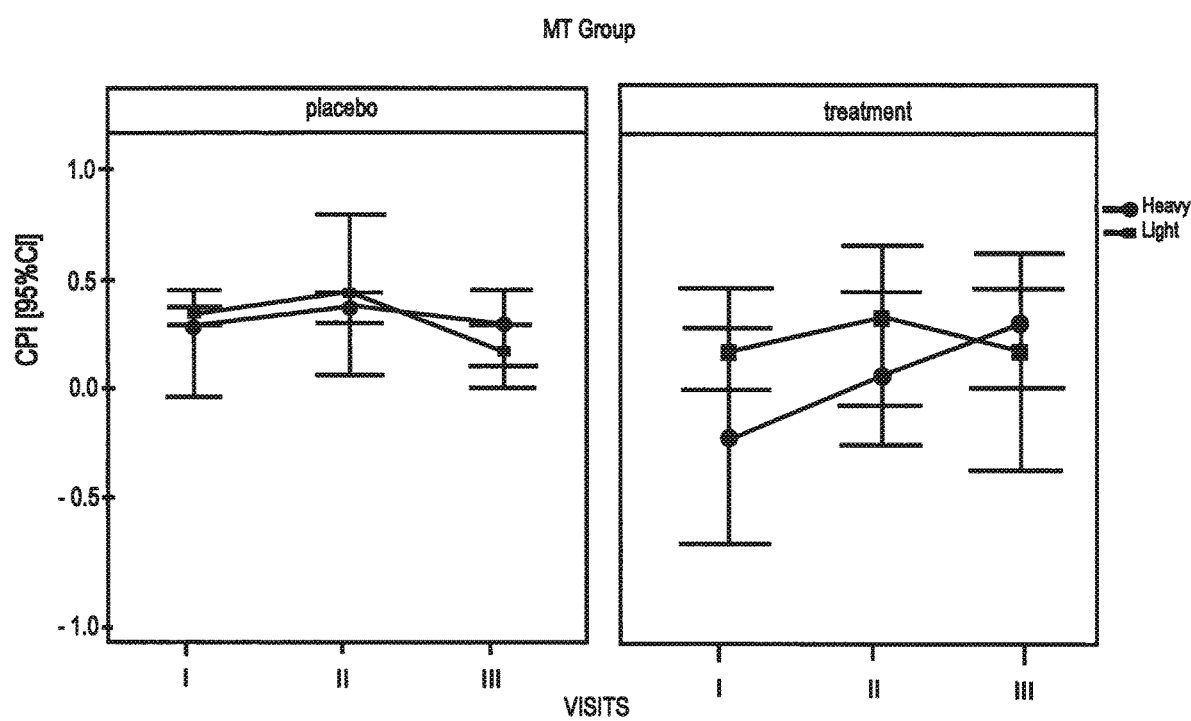
FIG. 4 is a graph showing changes in the values of CPI (Cognitive Performance Index), which is used to assess cognitive functions in the MT group.

FIG. 4 shows changes in the values of CPI, which is used to assess cognitive functions in the MT group.

The Conclusions of Neuropsychological Tests:

The neuropsychological (cognitive) part of the research suggests that COLOCO prp can, in a relatively short period of observation (16 weeks):

increase the efficiency of short-term visual memory in the oldest group, i.e. AAMI ("OLD"), as indicated by the DMS test results (variable: Percent Correct, Visit 1 vs Visit 3, $F=3.005$; $p=0.086$, $eta2=0.24$).

improve learning abilities and spatial memory in the youngest group—MT, as evidenced by the PAL test results (variable: Total errors adjusted, analysis of the intra-group effect; $F=5.072$; $p=0.007$, $eta2=0.43$).

increase the speed of reaction in response to a stimulus in the average group, i.e. ADT, as indicated by the RTI test results in the system of intergroup analysis (variable: Simple reaction time, reproducible intergroup analysis placebo vs. treatment, $F=2.793$; $p=0.097$, $eta2=0.24$).

positively influence the ability to focus (concentration), as indicated by the RVP test results (variable: RVP.A; Visit 1 vs Visit 3, $F=3.039$; $p=0.084$, $eta2=0.26$).

Biochemical Analysis:

In order to elucidate the precognitive properties of COLOCO prp, the concentration of the specific biomarker of brain activity, BDNF, was measured. BDNF has a prominent role in synaptic plasticity, induction of long-term potentiation (LTP) and neuronal differentiation and survival (neuroprotection). BDNF level was estimated in blood samples collected at Baseline (Visit 1) and at the end of the study (Visit 3).

Figure 5:
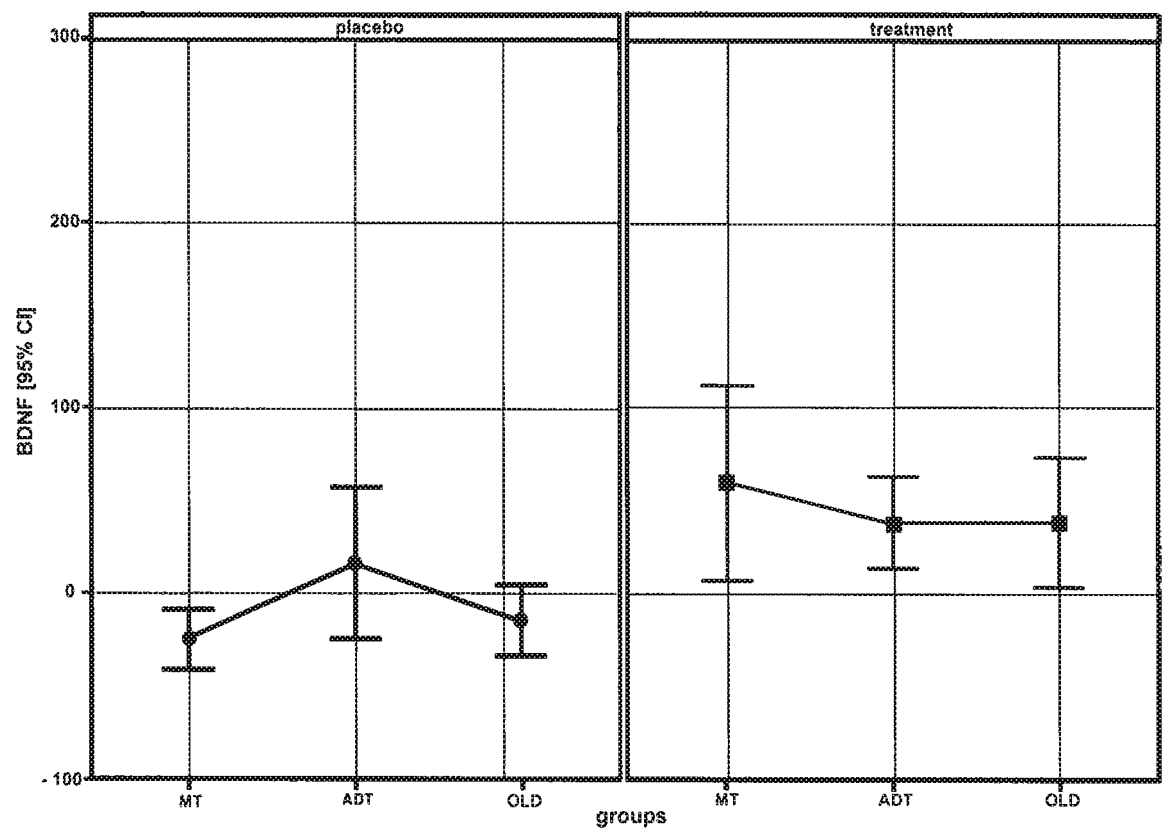
FIG. 5 is a graph showing Serum BDNF level in research subjects in respective age groups depending on the sex (MT-age ≥18 and ≤25; ADT-age >25 and ≤55; OLD-age >55 and ≤75), based on study results presented as a mean value and standard deviation with the 95% confidence intervals.

FIG. 5 is a graph showing the study results presented as a mean value and standard deviation with the 95% confidence intervals in the respective age groups along with the level of significance. Considering the age groups, in the MT, ADT and OLD group treated with COLOCO prp there was an increase of serum BDNF level in 78%, 44% and 62.5% of subjects, respectively. In control (Placebo) group, the level of BDNF was found higher in 18% of MT subjects, 23.5% of ADT subjects and 30% of OLD individuals. In addition, biochemical analysis revealed a significant drop in BDNF concentration in some participants. Serum BDNF level was reduced in 36.9% of subjects treated with COLOCO prp, and in 75.8% of subjects in the control group.

In Table 2, values of experimental groups are shown as mean values of percentages of treated and placebo groups. Results of the study revealed statistically significant higher level of BDNF ($F(1, 125)=27.2$; $p<0.001$, $eta2=0.55$) in serum of all participants treated with COLOCO prp in comparison to the Placebo group.

TABLE 2

Serum BDNF concentration of COLOCO prp treated subjects in relative to the control (Placebo) group.

| Change | Group | |
| --- | --- | --- |
| | Placebo | COLOCO prp |
| Deterioration | 47 [1] | 24 [1] |
| | 75.8% [2] | 36.9% [2] |
| Improvement | 15 [1] | 41 [1] |
| | 24.2% [2] | 63.1% [2] |
| Total | 62 [1] | 65 [1] |

[1] The number of participants with the improvement/deterioration/the same level of BDNF;
[2] the percentage of participants with the improvement/deterioration/the same level of BDNF in relative to all participants (n = 125).

In Table 3 are presented morphological test results. The percentage of lymphocytes in regard to the level of all white blood cells slightly differed between two experimental groups.

TABLE 3

Alteration of the percentage of lymphocytes in regard to the total level of white cells in the COLOCO prp treated group and in the Placebo group.

| Change | Grupa | |
|---|---|---|
| | Placebo | COLOCO prp |
| Deterioration | 11 [1] | 1 [1] |
| | 13% [2] | 1% [2] |
| Improvement | 5 [1] | 10 [1] |
| | 6% [2] | 13% [2] |
| The same | 66 [1] | 68 [1] |
| | 80% [2] | 86% [2] |

[1] The number of participants with the improvement/deterioration/the same level of lymphocytes;
[2] the percentage of participants with the improvement/deterioration/the same level of lymphocytes in relative to all participants (n = 125).

The Conclusions of Biochemical Analysis:

Biochemical analysis revealed an increase of BDNF level in 63.1% of subjects treated with COLOCO prp (chi2(1)= 19.46; $p<0.001$: OR=0.1868, 95% CI=0.0866-0.4031). In the COLOCO prp treated group, the level of lymphocytes return to the range of concentration considered as physiological level in 13% of subjects (chi2(2) =9.977; p=0.006814), indicating the ability of COLOCO prp to modulate and restore immunological system homeostasis.

During the final visit ending the study, all participants were asked to give the unexpected and unpleasant symptoms that might have appeared during the treatment None of patients who received COLOCO prp reported adverse effects, indicating that COLOCO prp can be safely used by humans.

Example 1

Pharmaceutical Composition (Tablets):

| Ingredient | mg |
|---|---|
| COLOCO prp | 0.12 |
| Lactose monohydrate DC | 100.00 |
| Lactose 200 mesh | 70.86 |
| Sorbitol | 270.00 |
| Microcrystalline cellulose | 69.00 |
| Xanthan gum | 6.00 |
| Vanilla flavour | 6.00 |
| Silicon dioxide | 3.00 |
| Magnesium stearate | 5.00 |
| Total | 530.00 |

Total weight of a tablet containing the following ingredients is 530 mg.

Infant Milk Formula Stage 1 Enriched with COLOCO Prp (GM-1C)

Formula milk stage 1 is an infant formula for babies 0-5 months, commercially available MAMI LAC 1, supplemented with COLOCO prp in the amount of 20 μg per 100 mg of the milk formula powder, providing the dose of COLOCO prp 2.7 μg per 100 ml of the ready to drink product

| Composition | | Per 100 ml of ready to drink product | 100 g |
|---|---|---|---|
| Energy | Kcal | 69 | 510 |
| | kJ | 290 | 2140 |
| Fat: | g | 3.5 | 25.5 |
| Linoleic acid | mg | 450 | 3300 |
| α-linolenic acid | mg | 61 | 450 |
| Protein: | g | 1.28 | 9.5 |
| Casein | g | 0.51 | 3.8 |
| Whey-protein | g | 0.77 | 5.7 |
| Carbohydrates: | g | 8.2 | 60.6 |
| Lactose | g | 7.4 | 54.8 |
| Maltodextrin | g | 0.8 | 5.8 |
| Moisture | g | | 3.0 |
| Vitamins: | | | |
| Vit. A | μg | 85 | 630 |
| Vit. D3 | μg | 1.4 | 10.5 |
| Vit. E | mg | 1.1 | 8.1 |
| Vit. K1 | μg | 4.1 | 30 |
| Vit. C | mg | 8.1 | 60 |
| Vit. Bi | μg | 58 | 430 |
| Vit. B2 | μg | 142 | 1050 |
| Vit. B6 | μg | 47 | 350 |
| Vit. B12 | μg | 0.15 | 1.1 |
| Niacin | mg | 0.69 | 5.1 |
| Folic acid | μg | 9.7 | 72 |
| Pantothenic acid | μg | 311 | 2300 |
| Biotin | μg | 1.5 | 11 |
| Minerals: | g | 0.32 | 2.4 |
| Calcium | mg | 56 | 415 |
| Phosphorus | mg | 28 | 210 |
| Magnesium | mg | 5.7 | 42 |
| Iron | mg | 0.76 | 5.6 |
| Zinc | mg | 0.46 | 3.4 |
| Manganese | μg | 8.3 | 61 |
| Copper | μg | 49 | 360 |
| Iodine | μg | 11 | 81 |
| Sodium | mg | 23 | 170 |
| Potassium | mg | 64 | 470 |
| Chlorine | mg | 45 | 335 |
| Selenium | μg | 2.1 | 15.40 |
| Choline | mg | 8.8 | 65 |
| Inositol | mg | 3.0 | 22 |
| Taurine | mg | 4.9 | 36 |
| L-carnitine | mg | 1.9 | 14 |
| COLOCO prp | μg | 2.7 | 20 |

Follow-on Milk Formula Stage 2 Enriched with COLOCO Prp (GM-2C)

Formula milk stage 2 is a follow-on formula for babies 6-12 months, commercially available MAMI LAC 2, supplemented with COLOCO prp in the amount of 40 μg per 100 mg of the milk formula powder, providing the dose of COLOCO prp 5.6 μg per 100 ml of the ready to drink product.

| Composition | | 100 ml of ready to drink product | 100 g |
|---|---|---|---|
| Energy | kcal | 69 | 485 |
| | kJ | 290 | 2040 |
| Fat: | g | 3.1 | 22.0 |
| Linoleic acid | mg | 400 | 2800 |
| α-linolenic acid | mg | 55 | 390 |
| Protein: | g | 11 | 12.2 |
| Casein | g | 1.0 | 7.3 |
| Whey-protein | g | 0.7 | 4.9 |
| Carbohydrates: | g | 8.5 | 59.8 |
| Lactose | g | 5.7 | 39.8 |
| Maltodextrin | g | 2.8 | 20.0 |
| Moisture | g | | 3.0 |
| Vitamins: | | | |
| Vit. A | μg | 73 | 512 |
| Vit. D3 | μg | 1.5 | 10.3 |

-continued

| Composition | | 100 ml of ready to drink product | 100 g |
|---|---|---|---|
| Vit. E | mg | 1.0 | 6.7 |
| Vit. K1 | μg | 5.4 | 38 |
| Vit. C | mg | 12.8 | 90 |
| Vit. B1 | μg | 71 | 500 |
| Vit. B2 | μg | 91 | 640 |
| Vit. B6 | μg | 50 | 350 |
| Vit. B12 | μg | 0.16 | 1.1 |
| Niacin | mg | 0.70 | 4.9 |
| Folic acid | μg | 11 | 78 |
| Pantothenic acid | μg | 370 | 2600 |
| Biotin | μg | 1.7 | 12 |
| Minerals: | g | 0.57 | 4.0 |
| Calcium | mg | 85 | 600 |
| Phosphorus | mg | 61 | 430 |
| Magnesium | mg | 8.3 | 58 |
| Iron | mg | 1.3 | 9.2 |
| Zinc | mg | 0.71 | 5.0 |
| Manganese | μg | 3.8 | 27 |
| Copper | μg | 51 | 360 |
| Iodine | μg | 12 | 81 |
| Sodium | mg | 31 | 220 |
| Potassium | mg | 110 | 771 |
| Chlorine | mg | 68 | 480 |
| Selenium | μg | 0.75 | 5.3 |
| Choline | mg | 14 | 95 |
| Taurine | mg | 7.1 | 50 |
| Inositol | mg | 6.8 | 48 |
| COLOCO prp | μg | 5.6 | 40 |

What is claimed is:

1. A method of treating disorders and conditions related to a decrease or fluctuations of a Brain-Derived Neurotrophic Factor (BDNF) level, said disorders and conditions comprising mild cognition deficit, depressed mood, memory decline, or concentration and memory difficulties, or pertaining to temporary intensive mental activity and tiredness, wherein BDNF diagnosed in a blood serum is a biomarker of said disorders and conditions, the method comprising administering a Proline-Rich Polypeptide complex to a subject in an amount effective to treat said disorders and conditions, the Proline-Rich Polypeptide complex having a molecular weight of up to 10 kDa comprising 16-22% of proline, derived from the mammalian colostrum.

2. The method according to claim 1, wherein administering comprises administering orally in the cases of low levels of the BDNF diagnosed in the blood serum.

3. The method according to claim 1, wherein the amount of the Proline-Rich Polypeptide complex administered is effective to increase the efficiency of short-term visual memory, improve learning abilities and spatial memory, increase the speed of reaction in response to a stimulus, improve the ability to focus and/or to concentrate.

4. The method according to claim 1, wherein the Proline-Rich Polypeptide complex is administered as a nutritional additive for older babies after breastfeeding, for children, and for adults.

5. The method according to claim 1, wherein the Proline-Rich Polypeptide complex is administered as a nutritional additive for pregnant women, in order to increase the BDNF level in the blood of a mother and a baby.

6. The method according to claim 1, wherein the Proline-Rich Polypeptide complex is administered as an additive in a Proline-Rich Polypeptide-enriched formula for older babies after breastfeeding, in order to increase the BDNF level in a baby blood.

7. The method according to claim 1, wherein the Proline-Rich Polypeptide complex is administered as an additive in an infant nutritional milk formula, in order to increase the BDNF level in an infant blood, to the level being at least comparable to the level detected in the blood of breastfed baby.

8. The method according to claim 7, wherein the Proline-Rich Polypeptide complex is administered as an additive in an infant nutritional milk formula, to nourish infants belonging to the group comprising infants who had not been breasted from birth and infants post weaning from mother's milk, said infants being additionally diagnosed with a low Brain-Derived Neurotrophic Factor level in the blood.

9. The method according to claim 1, wherein the Proline-Rich Polypeptide complex is isolated from the bovine or any other farm animal colostrum.

10. The method according to claim 1, wherein the Proline-Rich Polypeptide complex comprises about 18% of acidic amino acids.

11. The method according to claim 10, wherein the Proline-Rich Polypeptide complex is free of the β-lactoglobulin fraction.

12. The method according to claim 1, wherein the Proline-Rich Polypeptide complex is administered as a medicament formulated to provide a pharmaceutical composition, or is in the form of nutraceutic, nutritional supplement, food for a special medical purpose, food for particular nutritional uses or dietary supplement.

13. The method according to claim 12, wherein said medicament is comprising effectively daily dose of the Proline-Rich Polypeptide complex for adults within the range 50-1000 micrograms.

14. The method according to claim 13, wherein said effectively daily dose of the Proline-Rich Polypeptide complex is in the range 80-160 micrograms.

15. The method according to claim 12, wherein said medicament is formulated for pregnant women and comprising effectively daily dose of the Proline-Rich Polypeptide complex within the range 50-140 micrograms.

16. The method according to claim 12, wherein said medicament is formulated to be included in a Proline-Rich Polypeptide-enriched formula for infants to comprise about 20 micrograms of Proline-Rich Polypeptide complex per 100 g.

17. The method according to claim 12, wherein said medicament is formulated to be included in a Proline-Rich Polypeptide-enriched formula for infants in an amount sufficient to meet the daily infant's requirement for Proline-Rich Polypeptide complex within the range of 1 to 5 micrograms per 1 kilogram of body weight.

* * * * *